United States Patent
Konesky et al.

(10) Patent No.: US 10,595,924 B2
(45) Date of Patent: Mar. 24, 2020

(54) ELECTROSURGICAL SNARE DEVICE

(71) Applicant: Bovie Medical Corporation, Clearwater, FL (US)

(72) Inventors: Gregory A. Konesky, Hampton Bays, NY (US); Borislav S. Simeonov, St. Petersburg, FL (US); Shawn Roman, Safety Harbor, FL (US)

(73) Assignee: Apyx Medical Corporation, Clearwater, FL (US)

( * ) Notice: Subject to any disclaimer, the term of this patent is extended or adjusted under 35 U.S.C. 154(b) by 216 days.

(21) Appl. No.: 15/507,402

(22) PCT Filed: Sep. 3, 2015

(86) PCT No.: PCT/US2015/048281
§ 371 (c)(1),
(2) Date: Feb. 28, 2017

(87) PCT Pub. No.: WO2016/036927
PCT Pub. Date: Mar. 10, 2016

(65) Prior Publication Data
US 2017/0245909 A1 Aug. 31, 2017

Related U.S. Application Data

(60) Provisional application No. 62/046,289, filed on Sep. 5, 2014.

(51) Int. Cl.
*A61B 18/04* (2006.01)
*A61B 90/90* (2016.01)
(Continued)

(52) U.S. Cl.
CPC ............ *A61B 18/042* (2013.01); *A61B 90/90* (2016.02); *A61B 2017/00482* (2013.01);
(Continued)

(58) Field of Classification Search
CPC . A61B 18/042; A61B 90/90; A61B 2218/007; A61B 2018/141; A61B 17/221;
(Continued)

(56) References Cited

U.S. PATENT DOCUMENTS

| | | |
|---|---|---|
| 3,955,578 A | 5/1976 | Chamness et al. |
| 4,294,254 A | 10/1981 | Chamness |

(Continued)

FOREIGN PATENT DOCUMENTS

| | | |
|---|---|---|
| CN | 101843523 | 9/2010 |
| WO | WO03049631 | 6/2003 |

(Continued)

OTHER PUBLICATIONS

International Search Report and Written Opinion for PCT Application No. PCT/US15/48281; dated Dec. 4, 2015; sixteen (16) pages.
(Continued)

*Primary Examiner* — Jaymi E Della
*Assistant Examiner* — Rachel A. Vierra
(74) *Attorney, Agent, or Firm* — Gerald E. Hespos; Michael J. Porco; Adam Hotzoglou

(57) ABSTRACT

An electrosurgical snare device is provided which uses a flow of inert gas to assist in the cutting and sealing process of tissue, while substantially reducing the formation of eschar and collateral tissue damage. The electrosurgical device includes a housing having a longitudinal axis; a support shaft attached to a distal end of the housing, and an end effector coupled to a distal end of the support shaft. The end effector includes a tube including a plurality of apertures and an electrically conducting spring disposed around the tube, where a spacing of the coils of the spring coincides with a spacing of the plurality of apertures, wherein a gas assisted electrosurgical effect is formed at each of the plurality of apertures when an inert gas flows through the
(Continued)

tube and the spring is energized. The tube may be configured as a loop or snare.

14 Claims, 14 Drawing Sheets

(51) Int. Cl.
    *A61B 18/00*     (2006.01)
    *A61B 18/14*     (2006.01)
    *A61B 17/00*     (2006.01)

(52) U.S. Cl.
    CPC .............. *A61B 2018/0019* (2013.01); *A61B 2018/00178* (2013.01); *A61B 2018/00196* (2013.01); *A61B 2018/00202* (2013.01); *A61B 2018/00577* (2013.01); *A61B 2018/141* (2013.01); *A61B 2018/1435* (2013.01); *A61B 2018/1475* (2013.01); *A61B 2218/002* (2013.01); *A61B 2218/007* (2013.01)

(58) Field of Classification Search
    CPC .... A61B 17/32056; A61B 2017/00482; A61B 2018/0019; A61B 2018/00196; A61B 2018/00202; A61B 2018/00577; A61B 2018/1435; A61B 2018/1475; A61B 2218/002
    See application file for complete search history.

(56) References Cited

U.S. PATENT DOCUMENTS

| | | | |
|---|---|---|---|
| 5,078,716 A | | 1/1992 | Doll |
| 5,084,054 A | | 1/1992 | Bencini et al. |
| 5,088,997 A | | 2/1992 | Delahuerga et al. |
| 5,116,332 A | | 5/1992 | Lottick |
| 5,376,094 A | | 12/1994 | Kline |
| 5,400,267 A | * | 3/1995 | Denen ................ A61B 17/00 128/908 |
| 5,669,920 A | | 9/1997 | Conley et al. |
| 6,287,304 B1 | | 9/2001 | Eggers et al. |
| 6,352,539 B1 | | 3/2002 | Avellanet |
| 6,371,967 B1 | | 4/2002 | Long et al. |
| 6,453,906 B1 | | 9/2002 | Taylor et al. |
| 7,540,872 B2 | | 6/2009 | Schechter et al. |
| 7,608,087 B1 | * | 10/2009 | Addis ............. A61B 17/12109 604/528 |
| 8,696,663 B2 | | 4/2014 | Pardoll et al. |
| 9,498,238 B2 | * | 11/2016 | Smith ................ A61B 17/221 |
| 2001/0049524 A1 | | 12/2001 | Morgan et al. |
| 2002/0007204 A1 | | 1/2002 | Goode |
| 2006/0264928 A1 | | 11/2006 | Kornerup et al. |
| 2007/0034211 A1 | | 2/2007 | Hug et al. |
| 2007/0293874 A1 | | 12/2007 | Okada |
| 2008/0167661 A1 | | 7/2008 | Pardoll et al. |
| 2008/0221587 A1 | * | 9/2008 | Schwartz ............. A61B 17/221 606/113 |
| 2010/0070008 A1 | | 3/2010 | Parker et al. |
| 2010/0100091 A1 | | 4/2010 | Truckai |
| 2013/0237982 A1 | | 9/2013 | Rencher et al. |
| 2013/0296846 A1 | | 11/2013 | Canady et al. |
| 2014/0309524 A1 | * | 10/2014 | Vetter ................. A61B 18/149 600/424 |
| 2015/0257817 A1 | | 9/2015 | Zoran et al. |

FOREIGN PATENT DOCUMENTS

| | | |
|---|---|---|
| WO | WO2004110294 | 12/2004 |
| WO | WO2011137377 | 11/2011 |
| WO | WO2014053844 | 4/2014 |
| WO | WO2014172396 | 10/2014 |

OTHER PUBLICATIONS

English Machine Translation of Chinese Patent Application CN101843523, obtained from European Patent Office's website on Jan. 15, 2019, 9 pages.

* cited by examiner

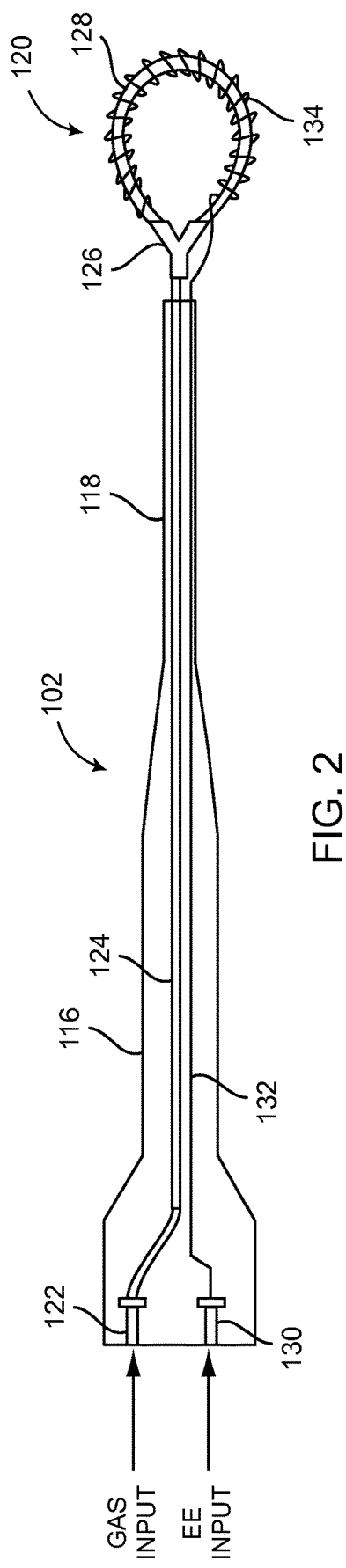

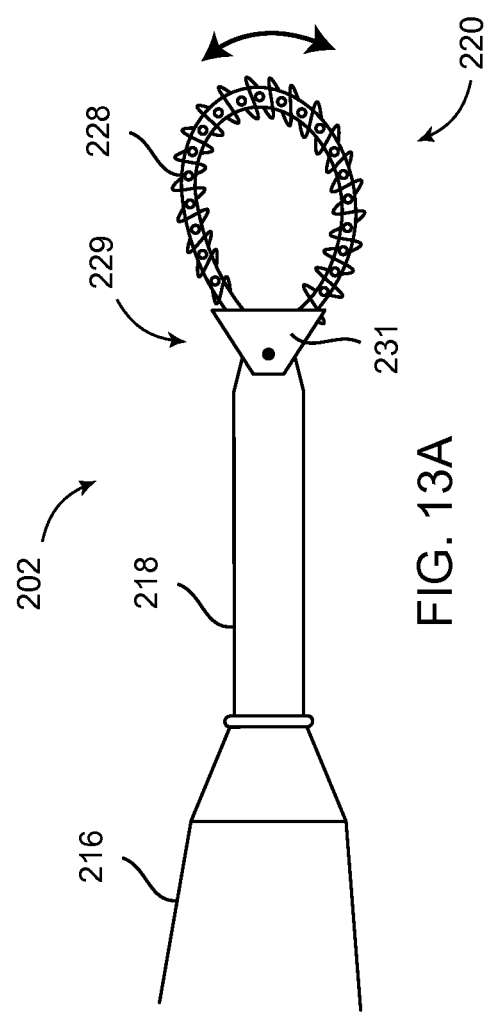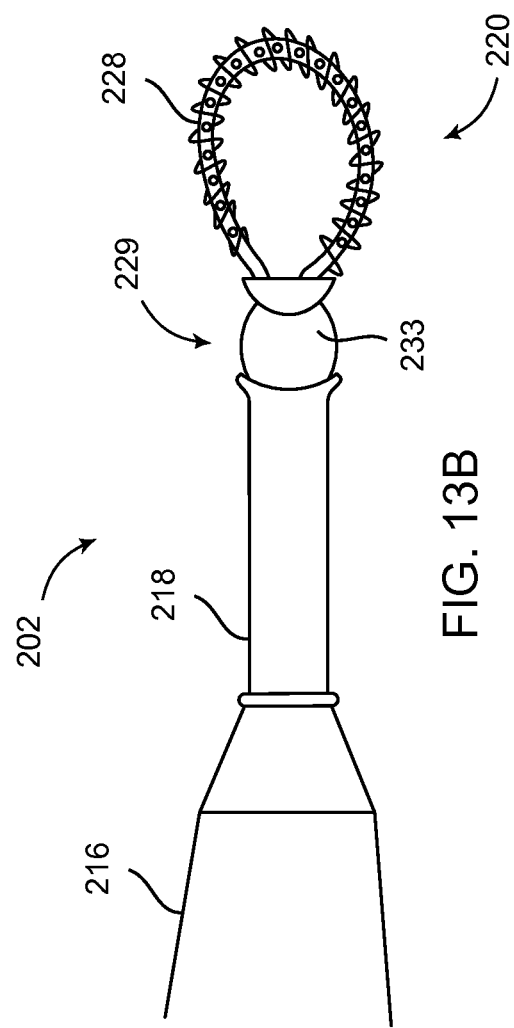

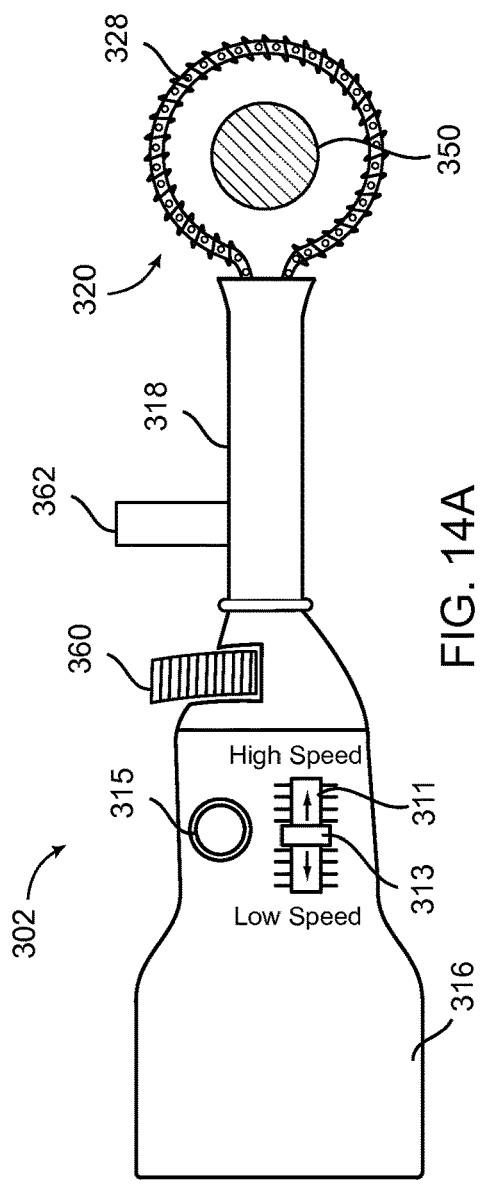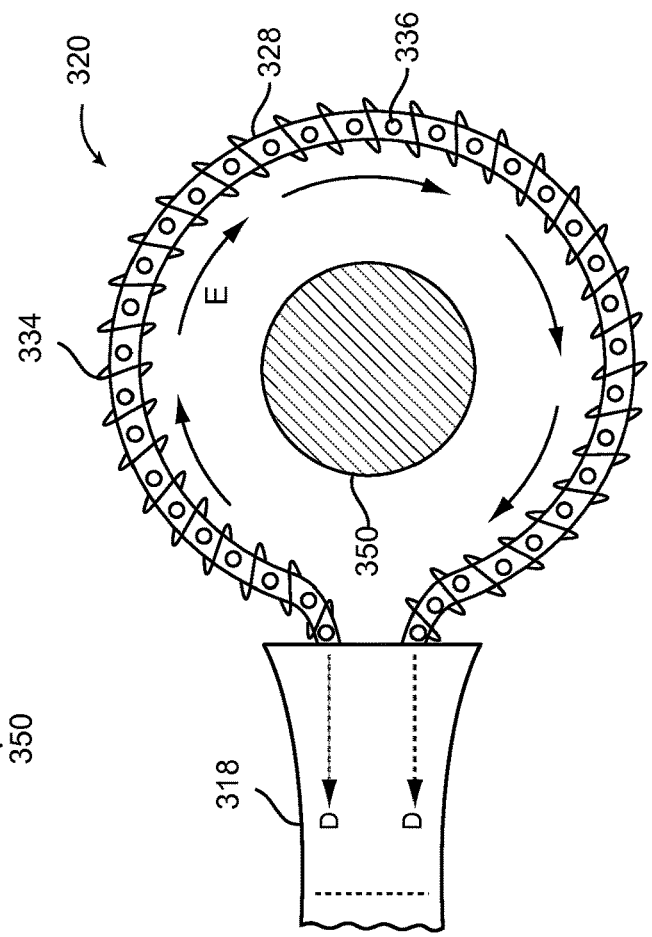

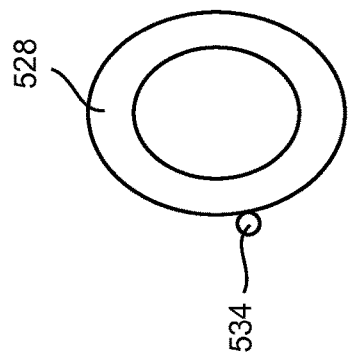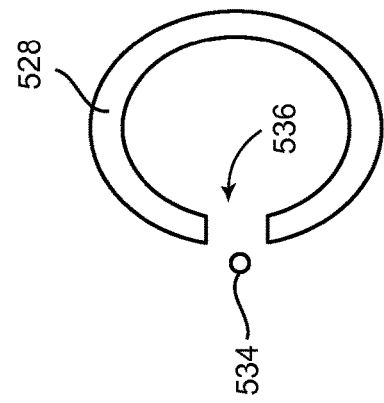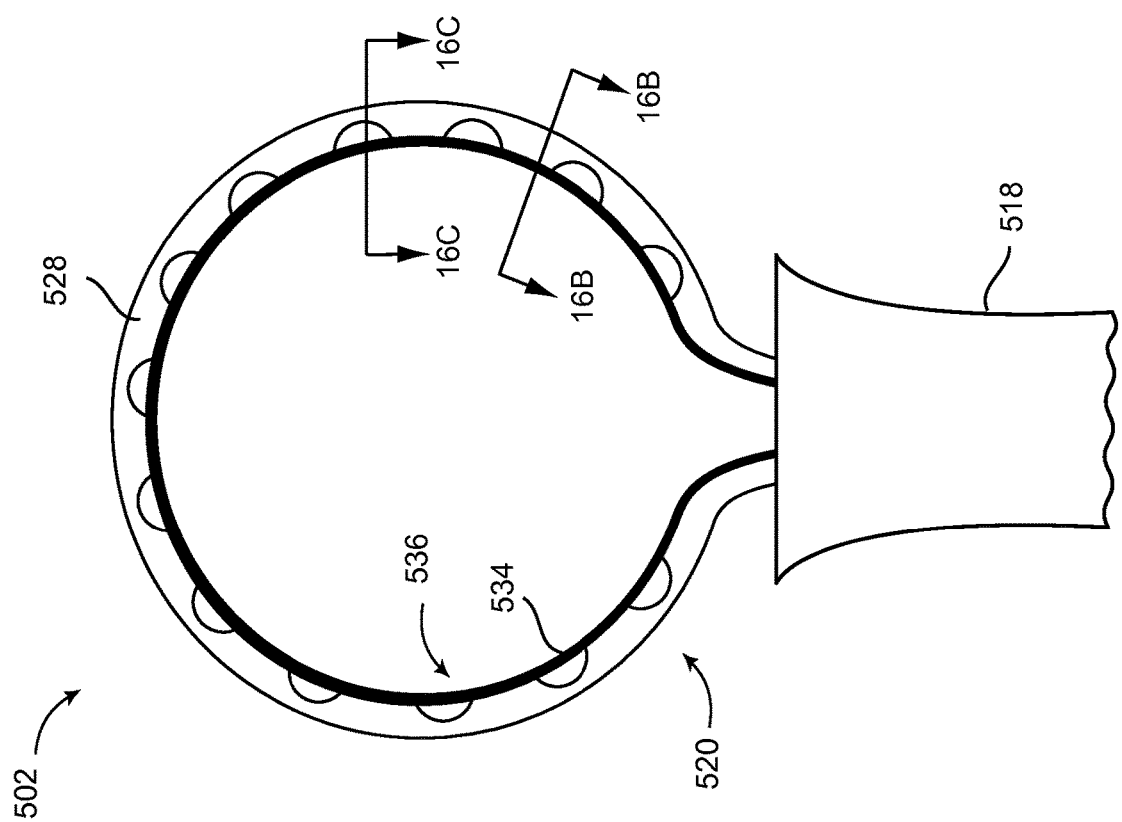

ELECTROSURGICAL SNARE DEVICE

PRIORITY

This application claims priority on U.S. Provisional Patent Appl. No. 62/046,289, filed Sep. 5, 2014, entitled "COLD PLASMA SNARE DEVICE", the contents of which are hereby incorporated by reference in its entirety.

BACKGROUND

Field

The present disclosure relates generally to electrosurgery and electrosurgical systems and apparatuses, and more particularly, to an electrosurgical snare device for removing polyps, tumors, or the like.

Description of the Related Art

Electrosurgical generators used in cutting and coagulating have become common place. Such devices include electrosurgical polyp snares for use in removing polyps found in the gastrointestinal tract. An electrosurgical snare uses a flexible small diameter wire to encircle a polyp or tumor, typically near its base. The snare is then electrically energized while it is drawn into a smaller and smaller diameter, progressively cutting through the polyp or tumor, and eventually severing it. The electrosurgical effect, in addition to cutting the tissue, also seals any fine blood vessels in the process. The flexible and small diameter nature of this snare makes it especially useful for endoscopic applications. An exemplary polyp snare is shown and described in commonly owned U.S. Pat. No. 8,696,663, the contents of which are hereby incorporated by reference.

However, use of conventional electrosurgical snares result in a relatively large amount of eschar at the surgical site and collateral damage to surrounding healthy tissue. Therefore, a need exists for techniques for removing polyps or tumors with relatively little or no eschar at the site of the polyp or tumor while minimizing collateral damage to surrounding healthy tissue.

SUMMARY

The present disclosure relates to an electrosurgical snare device for removing polyps, tumors, or the like.

An electrosurgical snare device is provided which uses a flow of inert gas to assist in the cutting and sealing process, while substantially reducing the formation of eschar and collateral tissue damage. The inert gas is supplied by a flexible, e.g., elastomeric, tube formed in a loop, or snare, where the tube is disposed inside a spring. The electrosurgical snare device employs a fine diameter spring of the compression-type, so that the inter-spring coils are always open. Alternately, an extension-type spring can be used, where a preloaded tension must be applied to open the inter-spring coils. The spring is connected to an electrosurgical generator which energizes the spring to provide the cutting and sealing energy.

A series of small diameter holes are placed along one side of the elastomeric tube, where the spacing of the holes coincides with the spacing of the coils of the spring. The flexible tube is positioned so that the holes are placed in the approximate center between adjacent coils, and aligned in the direction of cutting of the spring. Alternately, the tube can be rotated within the spring to adjust for various cutting directions. Inert gas can be supplied to one side of the elastomeric tube, where the other side is pinched off, or gas can be simultaneously supplied to both sides of the tube. The gas can be supplied by an electrosurgical generator which is also equipped with a gas control subsystem, or supplied by an external gas control device.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2 is a cross section view of an electrosurgical snare device in accordance with an embodiment of the present disclosure;

FIG. 3 is a close up view of an end effector of the electrosurgical snare device shown in FIG. 2;

FIG. 4 shows a close up view of the positioning of holes or apertures in an elastomeric tube with respect to individual coils of a cutting coil in accordance with an embodiment of the present disclosure;

FIG. 8A shows the electrosurgical snare disposed around a polyp or tumor, FIG. 8B shows the electrosurgical snare being drawn around the polyp or tumor, FIG. 8C shows the electrosurgical snare in contact with polyp and FIG. 8D shows completion of the cutting action by the electrosurgical snare;

FIG. 13A shows an electrosurgical snare device with an articulating mechanism in accordance with an embodiment of the present disclosure;

FIG. 13B shows an electrosurgical snare device with an articulating mechanism in accordance with another embodiment of the present disclosure;

FIG. 14A shows an electrosurgical snare device with a coil configured to move along a tube in accordance with an embodiment of the present disclosure;

FIG. 14B is a more detailed view of the electrosurgical snare device of FIG. 14A;

FIG. 16A shows an electrosurgical snare device, where the coil is on an outer wall of a tube in accordance with an embodiment of the present disclosure;

FIG. 16B is a cross-sectional view of a portion of the electrosurgical snare device of FIG. 16A;

FIG. 16C is another cross-sectional view of a portion of the electrosurgical snare device of FIG. 16A;

Figure 1:
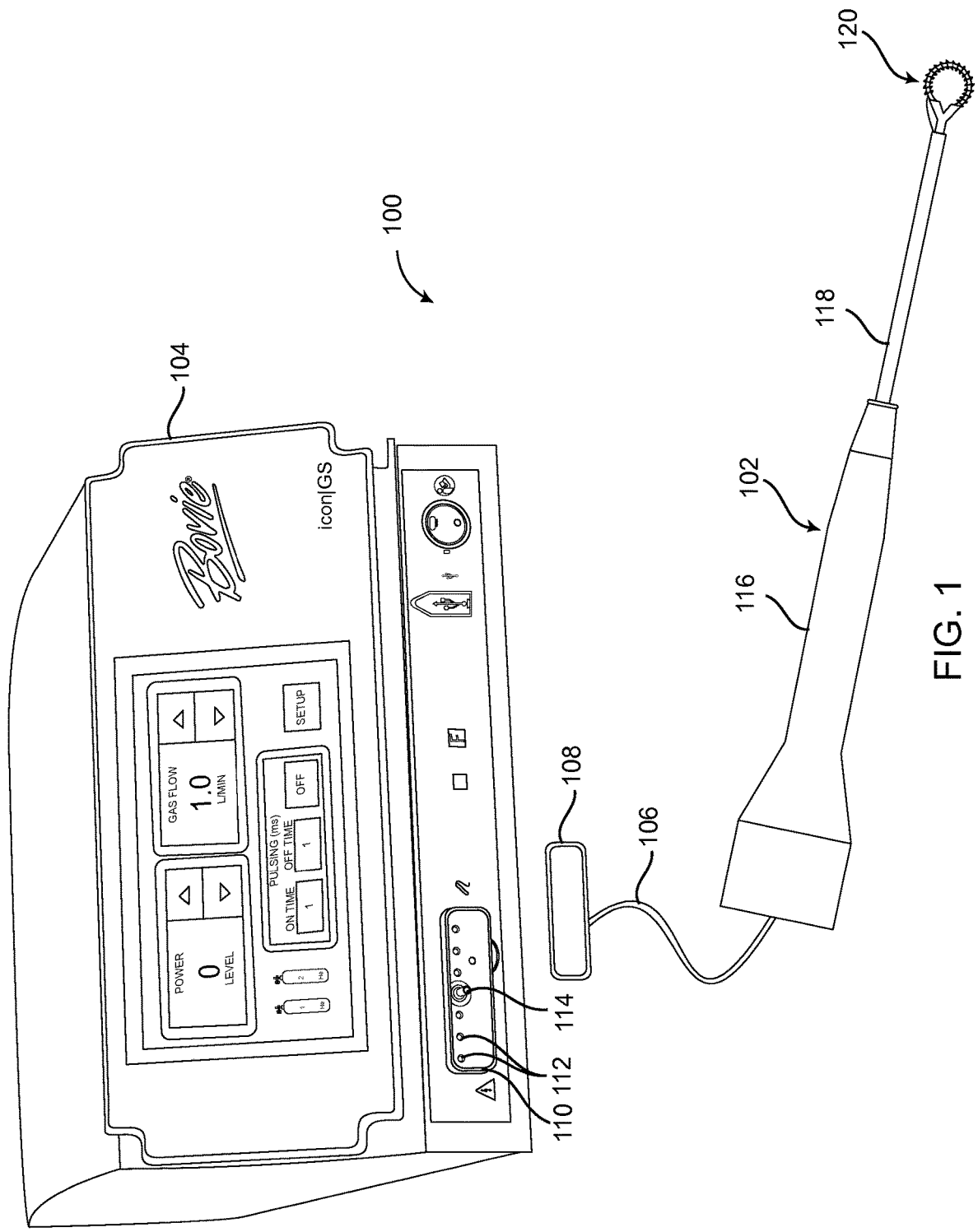
FIG. 1 is an illustration of an electrosurgical system including an electrosurgical snare device and an electrosurgical generator in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

In electrosurgery, the application of electrical energy to tissue, at moderately high voltage and high frequency, produces localized regions of plasma discharge. These discharges consist primarily of ionized air and ionized tissue debris. By contrast, atmospheric pressure cold plasma discharge jets utilize a stream of flowing gas, typically an inert gas such as helium or argon. Due to the required flow rates, typically liters per minute (LPM), other inert gases such as neon, krypton or xenon are far too expensive to be used at these flow rates. However, mixtures of helium or argon containing small amounts of these gases can be used economically. This gas, or mixture of gases, is ionized by passing it over a sharp point which is held at a somewhat higher voltage and high frequency. The ionized gas jet conveys electrical energy to the operative site. Typically, only a small portion of the gas jet is actually ionized. The flowing gas stream acts to both remove tissue debris and assist in cooling the operative site. A wide range of effect can be achieved by varying the ratio of electrical energy input to gas flow rate. A high electrical energy input and low gas flow rate, for example, a power level of 20 Watts and a flow rate of 1 LPM, will result in an intense ablative plasma jet, useful in removing tumors, for example. On the other hand, a low electrical energy input and high gas flow rate, for example, a power level of 5 Watts and a flow rate of 5 LPM, produces a mild plasma jet useful in sterilization or disinfection applications, without damaging the surface or material being sterilized.

A hybrid effect can be achieved using a combination of electrosurgery and an assisted inert gas flow. While not forming plasma jet discharges per se, the flowing gas both enhances the electrical discharge between the applicator and the operative site, and assists in carrying away excess heat. This results in substantial reduction in the formation of eschar and in the generation of collateral damage to surrounding healthy tissue. The use of helium for this gas assisted electrosurgical effect, also known as helium cooled RF, is particularly effective due to its high thermal conductivity.

A hybrid electrosurgical snare device is described which uses a flow of inert gas to assist in the cutting and sealing process of tissue, while substantially reducing the formation of eschar and collateral tissue damage. Rather than use a flexible wire, the electrosurgical snare device employs a fine diameter spring of the compression-type, so that the inter-spring coils are always open. Alternately, an extension-type spring can be used, where a preloaded tension must be applied to open the inter-spring coils. The spring is connected to an electrosurgical generator which energizes the spring to provide the cutting and sealing energy.

The inert gas is supplied by a flexible tube insert, e.g., an elastomeric tube insert, which fits inside the spring. A series of small diameter holes, e.g., vent holes, are placed along one side of the elastomeric tube, where the spacing of the holes coincides with the spacing of the coils of the spring. The elastomeric tube is positioned so that the holes are placed in the approximate center between adjacent coils, and aligned in the direction of cutting of the spring. Alternately, the tube can be rotated within the spring to adjust for various cutting directions. Inert gas can be supplied to one side of the elastomeric tube, where the other side is pinched off, or gas can be simultaneously supplied to both sides of the tube. The gas can be supplied by an electrosurgical generator which is also equipped with a gas control subsystem, or supplied by an external gas control device.

The gas flowing out of the vent holes assists in the electrosurgical effect, e.g., cutting and sealing of tissue, by supplementing the plasma discharge between the spring coils and the target tissue, and by carrying away excess heat from the operative site, reducing the formation of eschar and collateral damage to surrounding tissues.

Although certain embodiments are described in relation to removing a polyp or tumor, it is to be appreciated that the various embodiments of device of the present disclosure may be employed to affect other types of tissue, e.g., portion(s) of the uterus and/or kidneys, spleen, pancreas, gallbladder, remnant from liver, vascular aneurysm, etc.

FIG. 1 is an illustration of an electrosurgical system 100 including an electrosurgical snare device 102 and an electrosurgical generator 104 in accordance with an embodiment of the present disclosure. In one embodiment, a general purpose electrosurgical snare device 102 may be used for endoscopic applications. Note that while an endoscopic realization is shown, a shorter version could be used for open procedures.

The electrosurgical snare device 102 is coupled to an electrosurgical generator 104 equipped with gas flow control via cable 106 and appropriate connector 108. The electrosurgical generator 104 includes a corresponding receptacle 110 which includes electrical connections 112 to provide electrosurgical energy to the electrosurgical snare device 102 and a gas output connector 114 for providing gas to the electrosurgical snare device 102. It is to be appreciated that the cable 106 supplies both electrical power and gas flow and is coupled to the appropriate connectors on the electrosurgical snare 102, as shown in FIG. 2. In other embodiments, power and gas flow may be provided to the electrosurgical snare device 102 via separate sources.

Generally, the electrosurgical snare device 102 includes a handpiece or housing 116, an electrically non-conducting support tube or shaft 118 coupled to the handpiece 116 and an end effector 120 supported by the shaft 118. FIG. 2 is a cross section view of the electrosurgical polyp snare device 102 in accordance with an embodiment of the present disclosure. A gas input connector 122 is coupled to a tube 124 for providing, for example, an inert gas, to the end effector 120. The tube 124 is coupled to a gas manifold connector 126 which causes an elastomeric tube 128 to be formed into a loop. It is to be appreciated that materials other than elastomeric materials that are flexible enough to be configured as a loop may be employed. As will be described below, the tube 128 includes a plurality of holes or apertures 136 along one side for directing gas flow in a particular direction. An electrosurgical energy (EE) input connector 130 is coupled to conductor 132 for providing electrosurgical energy, e.g., radio frequency (RF) energy, to the end effector 120. At the end effector 120, the conductor 132 is formed into a helical coil 134 which is wound upon the tube 128. It is to be appreciated that the conductor 132 and coil 134 may be two separate components that may be joined by any conventional means or technique, for example, by wielding. It is further to be appreciated that cable 106 may be coupled to the connectors 122, 130 via various means.

A close-up view of the distal end of the electrosurgical snare applicator is shown in FIG. 3, where the positional relationships of the gas vent holes 136 and the spring coils 134 are shown in FIG. 4. As shown in FIG. 4, the holes or apertures 136 are positioned between portions of the coils 134 to allow gas flow without impediment. In one embodiment, the holes or apertures 136 are only in the region of the tube 128 where it is overlaid by the coil 134. Note that while an endoscopic realization is shown, a shorter version could be used for open procedures.

Figure 6:
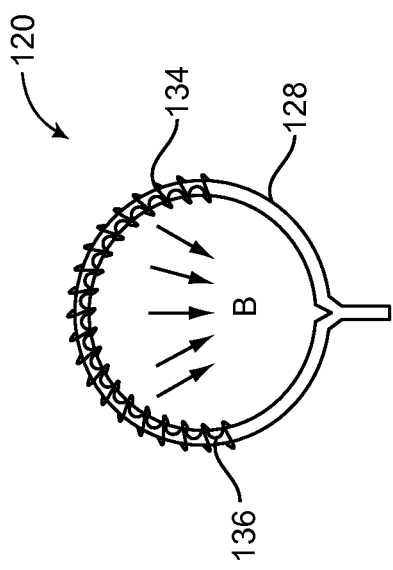
FIG. 6 shows the orientation of the gas vent holes for a "pulling" cutting direction in accordance with an embodiment of the present disclosure.
Figure 7:
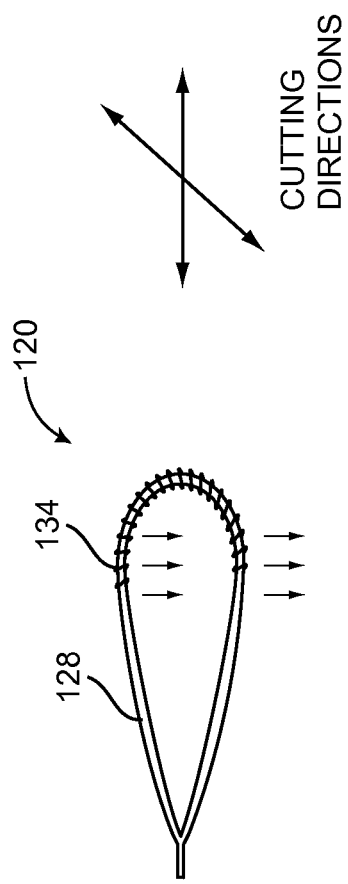
FIG. 7 shows the orientation of the gas vent holes for a surface-planing or "scraping" cutting direction in accordance with an embodiment of the present disclosure.
Figure 5:
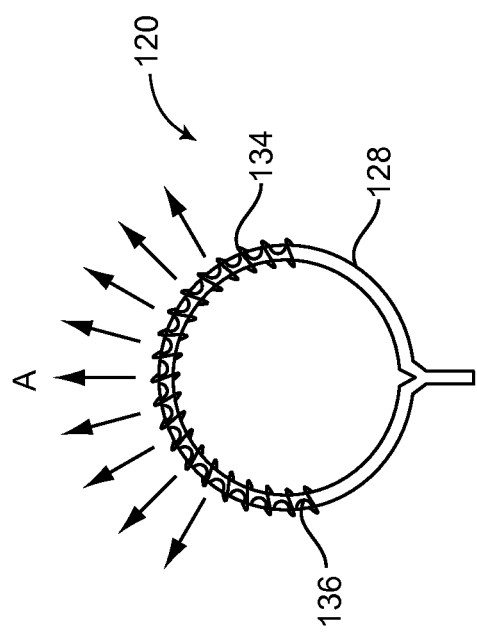
FIG. 5 shows the orientation of the gas vent holes for a "pushing" cutting direction in accordance with an embodiment of the present disclosure.

In addition to being used as a snare, the device 102 can be configured as a cold plasma version of an electrosurgical loop. In various embodiments, the holes are aligned in a particular direction to affect a desired cutting direction or effect. For example, referring to FIG. 5, the holes 136 face outward, and the cutting and sealing action is affected by pushing the device 102 forward as indicated by the arrows in direction A. Similarly, the holes can be aligned in an inward direction, as illustrated in FIG. 6, and the cutting action is affected by pulling the device, in the direction of arrows B, over the polyp, tumor or tissue to be removed. The holes can also be aligned so they are directed at right angles to the plane of the loop, as shown in FIG. 7, i.e., the holes or apertures 136 face downward toward the surgical site. This permits the surface of the tissue in the operative site to be planed-down, a layer at a time.

Figure 8B:
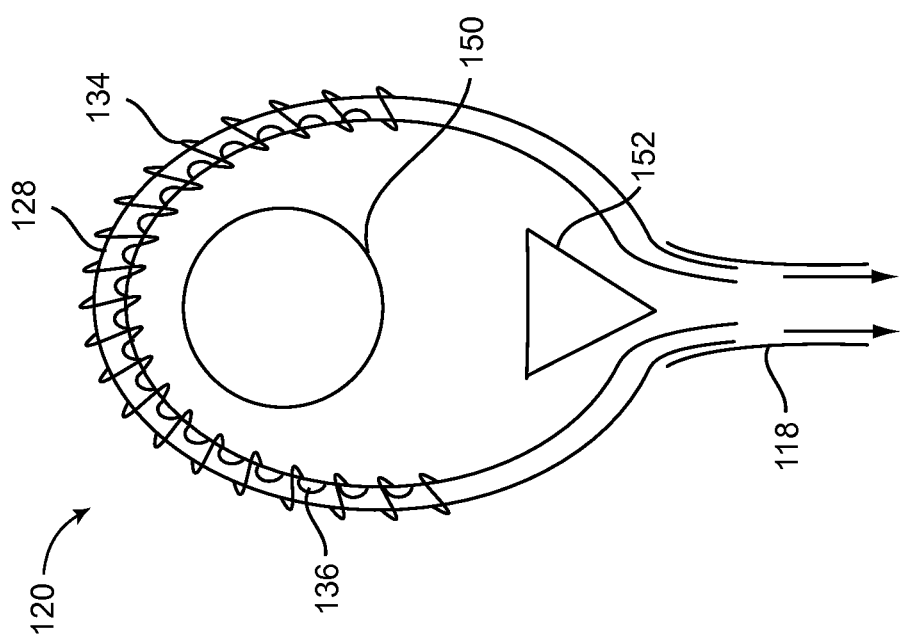
FIGS. 8A-8D illustrate a method for removing a polyp or tumor with an electrosurgical snare device in accordance with an embodiment of the present disclosure, where
Figure 8A:
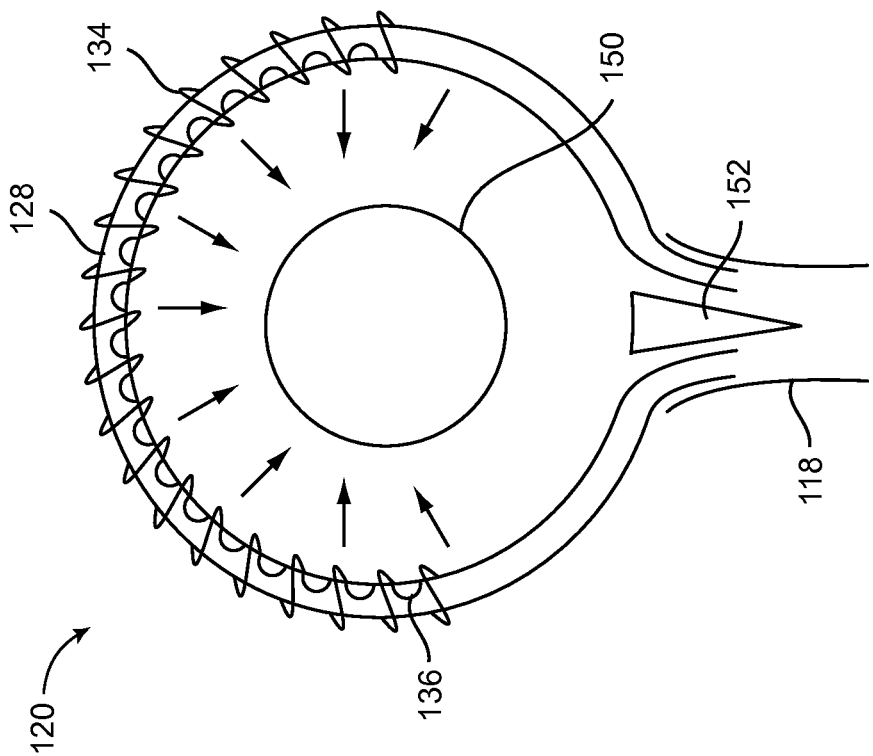
Figure 8D:
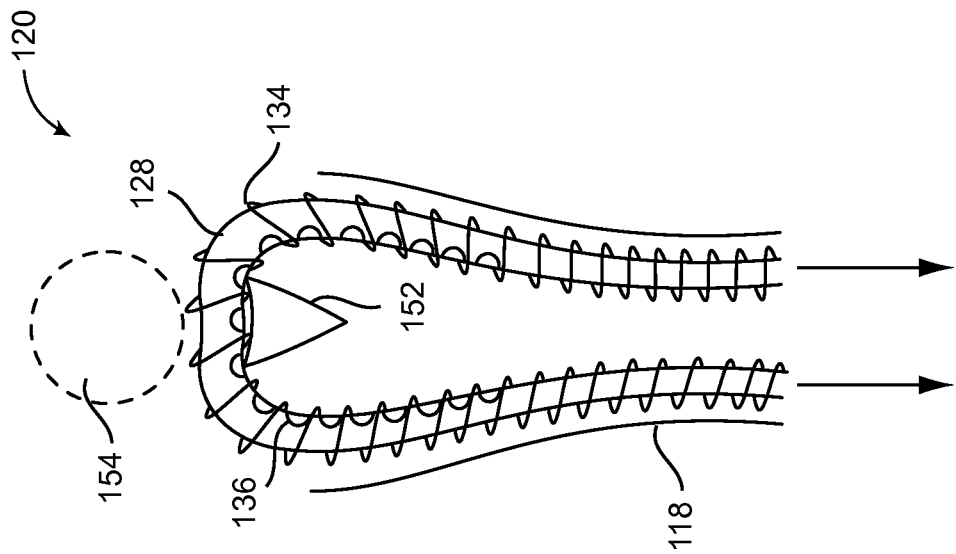

The use of the device 102 as a snare is illustrated in FIGS. 8A through 8D. In FIG. 8A, the extended end effector 120 is placed over a polyp or tumor 150, gas flow is initiated, and the cutting spring 134 is energized to creating an inert gas flow assisted electrosurgical effect. It is to be appreciated that the application of electrosurgical energy, e.g., RF energy, to the cutting spring may be initated by an activation button on the handpiece or housing 116, or alternatively, by a footswitch. Furthermore, a remote or auxiliary switch assembly may be provided including various buttons for controlling the handpiece or generator. Such a remote or auxiliary switch assembly is shown and described in commonly owned U.S. Pat. No. 8,696,663.

FIG. 8B shows the end effector 120 being drawn in around the polyp or tumor 150. It is to be appreciated that the end effector 120 may be drawn in, i.e., the loop made smaller, by various means. For example, in one embodiment, an actuator, e.g., lever, is coupled to tube 124 and moved along a longitudinal axis of the handpiece 116 to draw the end effector in tube 118. In another embodiment, the shaft 118 may be extended to achieve the same effect. Other methods for controlling the size of the snare or loop are contemplated to be within the scope of the present disclosure. For example, the tube 124 and/or coil 134 may be driven by a drive motor or positioning assembly as shown and described in commonly owned U.S. Pat. No. 8,696,663.

Figure 8C:
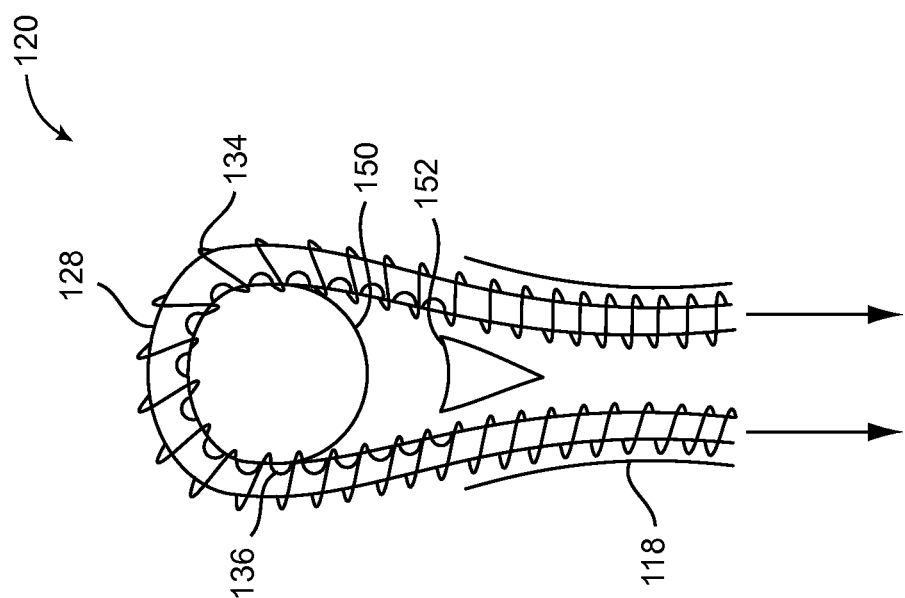

In FIG. 8C, the cutting action begins as the end effector 120 continues to be drawn in. In one embodiment, a back stop 152 is provided in the tube 118 to prevent the polyp or tumor from entering the tube. Finally, in FIG. 8D, the cutting action is complete, and the snare comes to a rest against the back stop 152. The polyp or tumor 150 is removed leaving the operative site 154 with little or no eschar. Gas flow then ceases and the cutting spring 134 is de-energized.

Figure 9:
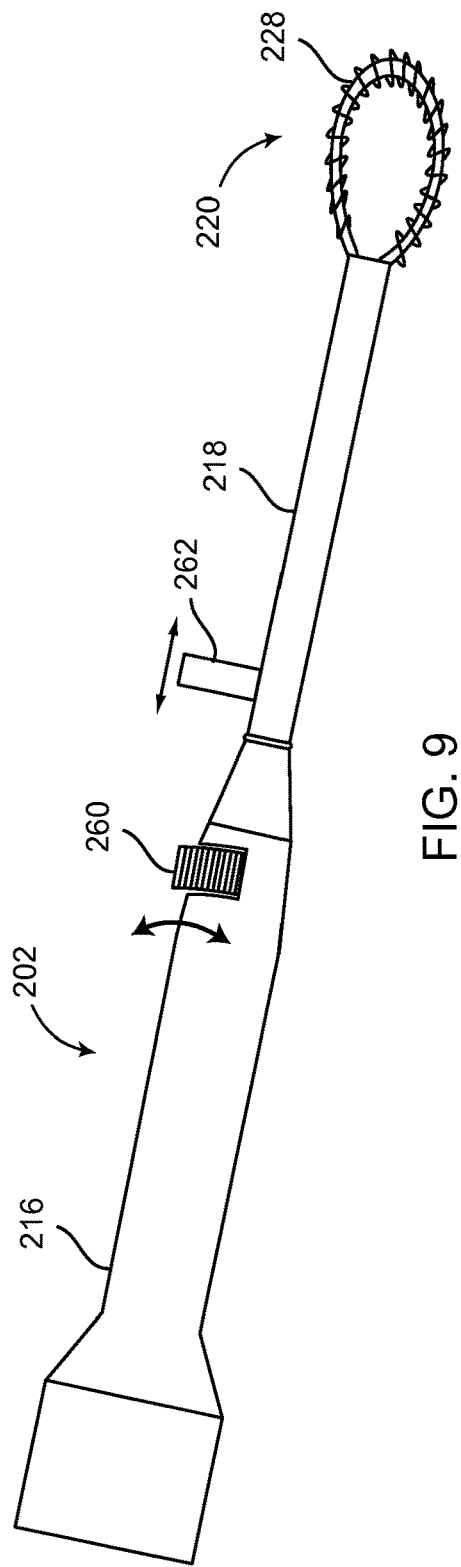
FIG. 9 shows an electrosurgical snare device with a rotatable tube to enable cutting in various directions in accordance with another embodiment of the present disclosure.
Figure 10:
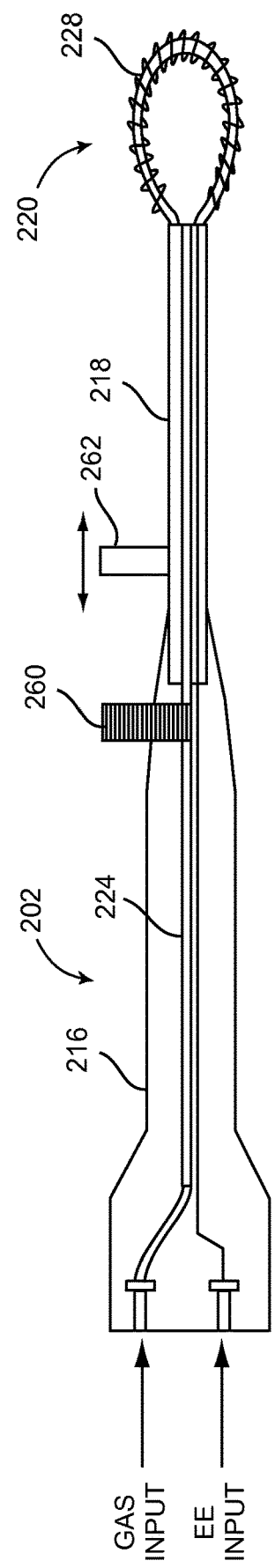
FIG. 10 is a cross sectional view of the electrosurgical snare device shown in FIG. 9.
Figure 11:
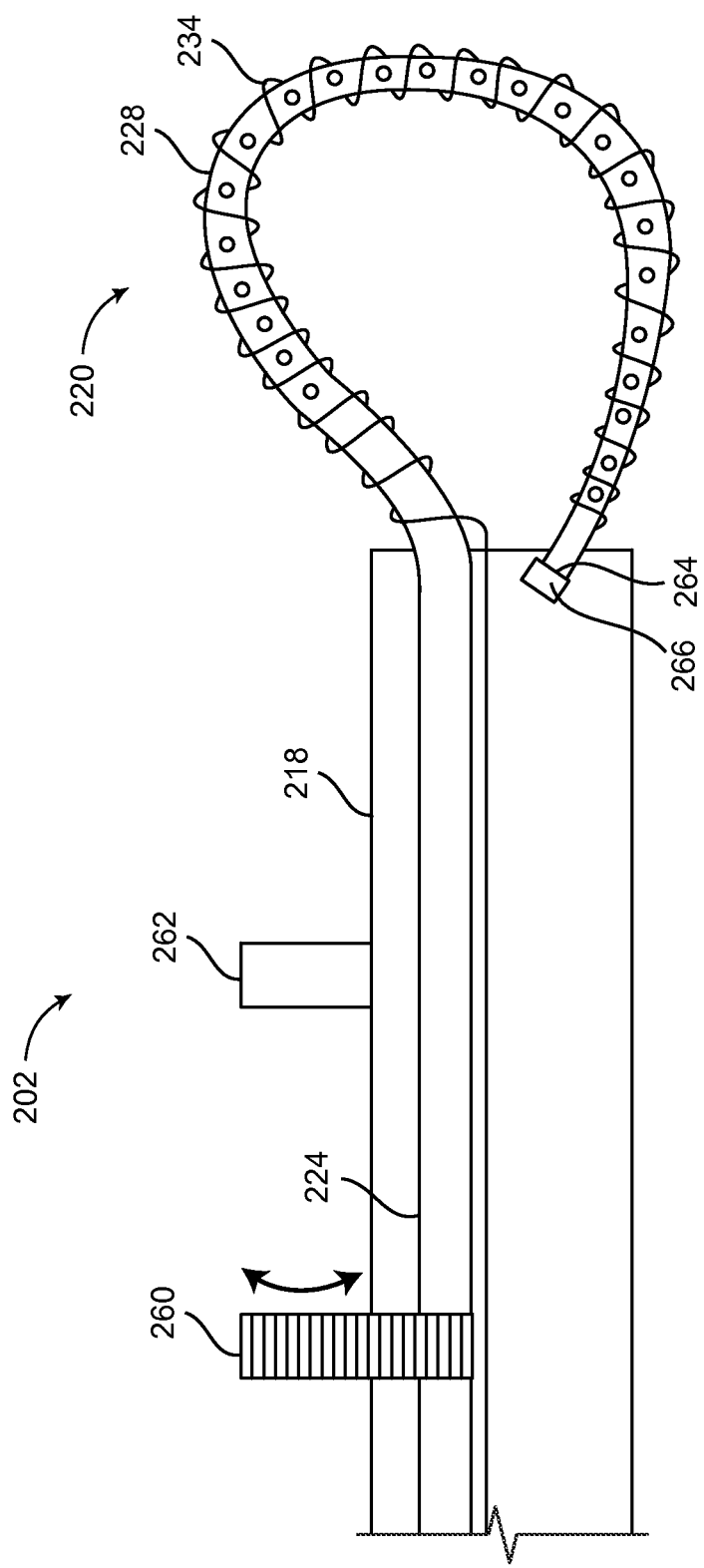
FIG. 11 is a close up view of the end effector of the electrosurgical snare device shown in FIGS. 9 and 10.

In FIGS. 9 through 11, a snare device 202 is illustrated where the orientation of the gas vent holes can be rotated to realize any of the functions shown in FIGS. 5 through 8D. FIG. 9 shows an electrosurgical snare device 202 with a rotatable tube to enable cutting in various directions. The device 202 includes a lever or thumbwheel 260 coupled to tube 224 to change position of the holes in the tube 228. This affects the rotation of the tube, and thereby the direction that the gas vent holes will point from inside the cutting spring 234.

In one embodiment, a second lever 262 is provided to extend or retract a telescopic tube or shaft 218. When extended, the shaft 218 is extended and the loop is made smaller; when the shaft 218 is retracted toward handpiece 216, the loop is made larger. The entire assembly of tube and spring can be extended or retracted from the applicator handle using the lever 262 shown in FIGS. 9 through 11. Also, a telescopic tube can be used between the electrosurgical snare end and the applicator handle 216 so that the overall device be can shortened for open procedures, or extended for endoscopic procedures.

FIG. 11 is a close up view of the end effector 220 of the electrosurgical snare shown in FIGS. 9 and 10. In this embodiment, the tube 228 has a closed end 264 which is anchored in the device, e.g., in the shaft 218. The anchor 266 may be rotatable to enable the tube 228 to be rotated.

It is to be appreciated that the end effector 220 may be drawn in, i.e., the loop made smaller, by various means. For example, in one embodiment, a lever, e.g., lever 262, is coupled to tube 224 and moved along a longitudinal axis of the handpiece to draw tube 228 into tube or shaft 218 while the closed end 264 remains anchored, thus making the loop smaller. Other methods for expanding and contracting the size of the loop are contemplated to be within the scope of the present disclosure.

Figure 12:
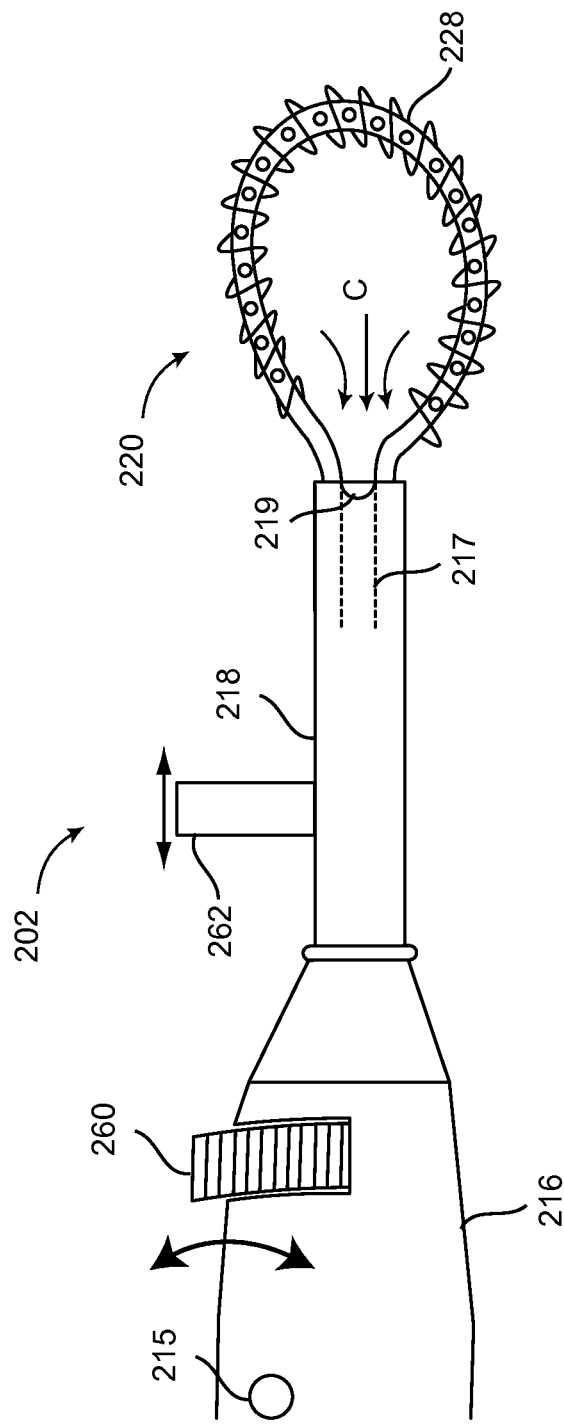
FIG. 12 shows an electrosurgical snare device with a suction port to enable suction of debris present during cutting in accordance with another embodiment of the present disclosure.

In an alternative embodiment, electrosurgical snare device 202 may include a central aspiration port for removal of debris, e.g., liquids, gases, etc., created and/or present at the operative site during procedures using the electrosurgical snare device 202. For example, referring to FIG. 12, electrosurgical snare device 202 is shown in accordance with the present disclosure including a central aspiration lumen 217 terminating with an apiration port 219 at the distal end of the device. Central aspiration lumen 217 is disposed in support tube 218. Furthermore, central aspiration lumen 217 is coupled to a suction input (not shown), where the suction input is coupled to applicator handle 216 of electrosurgical snare device 202. It is to be appreciated that the suction input is further coupled to a suction device (not shown), where the suction device may be part of the electrosurgical generator or may be an external device.

Furthermore, it is to be appreciated that, in some embodiments, electrosurgical snare device 202 includes a button or switch 215 for activating a suction device, where button or switch 215 may be disposed on applicator handle 216. In this way, when the button or switch 215 is pressed, the suction device will provide suction to aspiration lumen 217, where the suction provided to aspiration lumen 217 will draw debris present at the operative site during procedures using electrosurgical snare device 202 in a direction C towards aspiration port 219. Any debris drawn to aspiration port 219 will enter aspiration lumen 217 and be transported to a location away from the operative site.

It is to be appreciated that in certain embodiments, suction is supplied simultaneously while the gas assisted electrosurgical effect is in operation, i.e., during the application of electrosurgical energy. In other embodiments, the electrosurgical snare device will alternate between the application of electrosurgical energy and application of suction. In other embodiments, the electrosurgical snare device may include multiple lumens (not shown), for example, a first lumen for applying suction adjacent the end effector and a second lumen for irrigating the surgical site. It is to be appreciated that the irrigating medium may include liquids, gases and the like.

In yet another embodiment, electrosurgical snare device 202 may be configured such that the snare portion or end effector 220 can be articulated in various directions. In endoscopic applications, the use of a trocar limits sideways motion, which can be compensated for by an articulated tip. Articulation can also be used while cutting to provide for more complex ablation geometries. For example, referring to FIGS. 13A-B, electrosurgical snare device 202 is shown with an articulating mechanism 229. Specifically, referring to FIG. 13A, articulating mechanism 229 may be a hinge, joint or the like disposed on a distal end of support shaft 218 opposite to applicator handle 216. In one embodiment, the articulating mechanism 229 in FIG. 13A is a hinge 231 that is configured to allow tube 228 to move in a left to right or side-to-side motion. It is to be appreciated that in other embodiments articulating mechanism 229 may be a hinge that is configured to move in other planar motions. It is to be appreciated that the articulating mechanism 229 in the embodiment of electrosurgical snare device 202 shown in FIG. 13A may be controlled in various ways. In some embodiments, articulating mechanism 229 may be controlled via buttons that activate a motorized mechanism. For example, electrosurgical snare device 202 shown in FIG. 13A may have two buttons or switches disposed on applicator handle 216, where one button/switch is a left button causing a motor to move tube 228 to the left and another button/switch is a right button causing a motor to move tube 228 to the right. In some embodiments, the motor is disposed in applicator handle 216.

In another embodiment, the articulating mechanism 229 shown in FIG. 13A may be controlled via a pulley system. For example, springs may bias tube 228 towards one direction (e.g., left, right, up, or down) and a button or switch disposed on applicator handle 216 may cause the pulley to be pulled when the button or switch is pressed. When the pulley is pulled, tube 228 will move in a planar motion in a direction opposite to the direction which tube 228 was originally being bias by the spring.

It is to be appreciated that in another embodiment, articulating mechanism 229 may be configured to move end effector 220 freely in any direction. For example, referring to an embodiment of electrosurgical snare device 202 shown in FIG. 13B, an articulating mechanism 229, which allows tube 228 to be rotated in any direction, is configured as a ball joint 233. It should also be appreciated that while articulation could be affected by moving tube 228, the overall effect is to articulate the entire end effector 220 as a whole.

In the embodiments shown in FIGS. 1-13, the helical coils wound upon tubes 128 and 228 are stationary. In other words, the position of the coil relative to tubes 128 and 228 and/or vent holes or apertures 136 is not altered. However, it is to be appreciated that in other embodiments of the present disclosure the helical coils wound upon tubes 128 and 228 may be configured to move along tubes 128 and 228 as tubes 128 and 228 are drawn in to remove a polyp or tumor. For example, turning to FIGS. 14A-B, an electrosurgical snare device 302 is shown in accordance with an embodiment of the present disclosure, where a coil 334 is configured to move along tube 328 on electrosurgical snare device 302 as will be described in greater detail below.

Electrosurgical snare device 302 includes an applicator handle 316 coupled to a support tube or shaft 318. Shaft 318 supports end effector 320 which includes tube 328. Tube 328 includes holes or apertures 336. Coil 334 is wound around tube 328. Additionally, button 315 and thumbwheel 360 are disposed on applicator handle 316 and lever 362 is disposed on shaft 318.

Similar to previous embodiments, electrosurgical snare device 302 is configured such that inert gas flows through tube 328 and out of apertures 336. Electrosurgical energy can be applied to the inert gas exiting apertures 336 via coil 334 to produce an electrosurgical effect as described above. Additionally, thumbwheel 360 may be rotated to turn apertures 336 on tube 328 in a desired direction. Also, lever 362 may be positioned in a direction towards applicator handle 316 to increase the diameter of the loop formed by tube 328 or alternatively in a direction toward tube 328 to draw tube 328 into tube 318 to remove a polyp or tumor 350. Additionally, an automated positioning assembly may be provided to move move the loop between and extended position and a retracted position.

In contrast to previous embodiments, when button 315 is pressed, electrosurgical snare device 302 is configured such that coil 334 will move along tube 328, for example, in a direction E, as indicated in FIG. 14B. It is to be appreciated, that in some embodiments, when button 315 is pressed, electrosurgical snare device 302 is configured such that coil 334 will move along tube 328 continuously in one direction (e.g. direction E), while in another embodiment when button 315 is pressed, electrosurgical snare device 302 is configured such that coil 334 will oscillate between moving clockwise along tube 328 (as shown in FIG. 14B) and counter-clockwise along tube 328. A mechanism to affect the coil motion can take forms similar to that used to affect articulation as described above. Furthermore, the mechanism to affect coil motion may include an oscillating motor, e.g., a DC motor, piezoelectric motor, etc., disposed in the housing or handpiece 316 and coupled to the coil 334.

It is to be appreciated that in some embodiments, electrosurgical snare device 302 will include means for controlling the speed with which coil 334 moves or oscillates along tube 328. For example, in one embodiment, a selector 313 is disposed on applicator handle 316, as shown in FIG. 14A. Selector 313 may be pulled/pushed along a track 311 to achieve a desired location along track 311, where the position of selector 313 on the track 311 will determine the speed with which coil 334 moves or oscillates along tube 328. For example, when selector 313 is moved along track 311 in a direction toward tube 328 the speed with which coil 334 moves or oscillates along tube 328 will be increased. Additionally, when selector 313 is moved along track 311 in a direction away from tube 328 the speed with which coil 334 moves or oscillates along tube 328 will be decreased. It is to be appreciated that other means for controlling the speed of coil 334 are contemplated to be within the scope of the present disclosure, including but not limited to, buttons, thumbwheels, switches, etc.

It is to be appreciated that as coil 334 moves along tube 328, at different points in time, coil 334 will be disposed directly over an aperture 336 or between an aperture 336. When coil 334 is directly over an aperture 336, an enhanced gas assisted electrosurgical effect will be created because coil 334 will apply electrosurgical energy directly to the inert gas exiting aperture 336. Alternatively, when coil 334 is in between apertures 336, a reduced gas assisted electrosurgical effect will be created because less electrosurgical energy is being applied to the inert gas exiting aperture 336, since coil 334 is not directly over aperture 336. In this way, when button 315 is pressed (causing coil 334 to move along tube 328 as shown in FIG. 14B), there will be different local gas assisted electrosurgical effects at different points along tube 328 at different times. Furthermore, at any given point on tube 328, the local gas assisted electrosurgical effect will alternate between enhanced and reduced effects as coil 334 periodically passes over apertures 336.

The embodiment shown in FIGS. 14A and 14B and described above has several advantages. For example, in use, tube 328 will be placed around polyp or tumor 350 as shown in FIGS. 14A and B. Then, the user of electrosurgical snare device 302 will simultaneously position the lever 362 to grasp the polyp or tumor and press button 315. By positioning lever 362 and pressing button 315 simultaneously, tube 328 will be drawn in around polyp 350 while coil 334 is moving around tube 328. As stated above, the configuration shown in FIGS. 14A and 14B produces a periodically changing strength of the gas assisted electrosurgical effect at different point along tube 328. As a result of the periodically changing strength of this effect at any given point on tube 328, collateral damage to the surrounding healthy tissue is reduced as polyp or tumor 350 is removed. Also, the periodically changing strength of the gas assisted electrosurgical effect at any given point produces a smoother cutting process as polyp 350 is removed. Additionally, as tube 328 is drawn in around polyp 350 and coil 334 is moving around tube 328, coil 334 will be touching the tissue surface of polyp or tumor 350 and mechanically removing the material build up that accumulates during the removal of the polyp.

Figure 15B:
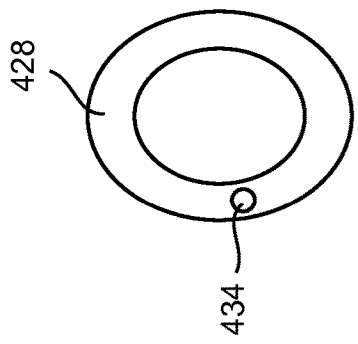
FIG. 15B is a cross-sectional view of a portion of the electrosurgical snare device of FIG. 15A.
Figure 15C:
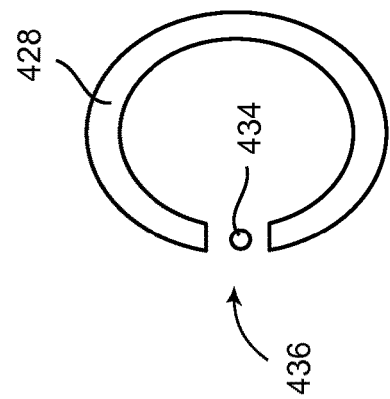
FIG. 15C is another cross-sectional view of a portion of the electrosurgical snare device of FIG. 15A.
Figure 15A:
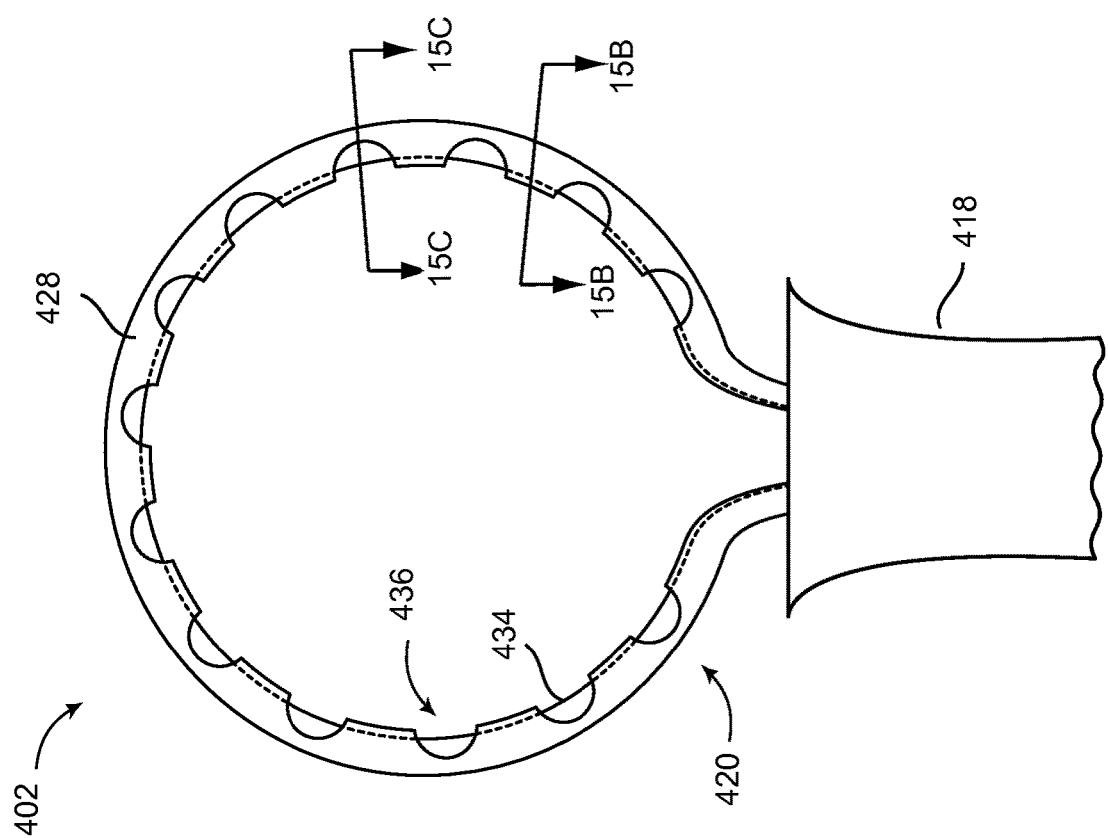
FIG. 15A shows an electrosurgical snare device, where the coil is embedded in an inner wall of a tube in accordance with an embodiment of the present disclosure.

Turning to FIG. 15A, an alternative embodiment of an electrosurgical snare device 402 is shown in accordance with the present disclosure. Similar to the embodiments described above, electrosurgical snare device 402 includes an applicator handle (not shown) coupled to a support tube or shaft 418. Shaft 418 supports end effector 420 which includes tube 428, where tube 428 includes apertures 436. As in the above described embodiments, electrosurgical snare device 402 is configured such that inert gas is provided to tube 428. However, in contrast to previously described embodiments, electrosurgical snare device 402 does not have a coil wrapping around tube 428; instead, electrosurgical snare device 402 includes a flexible coil or wire 434 embedded in the inner walls of tube 428. Coil or wire 434 is coupled to an electrosurgical energy source and is capable of conducting electrosurgical energy.

Turning to FIG. 15B, a cross-sectional view of tube 428 at the portion of tube 428 indicated by reference number 15B-15B in FIG. 15A is shown in accordance with the present disclosure. As shown in FIG. 15B, coil or wire 434 is embedded within the inner walls of tube 428. While in the inner walls of tube 428, coil or wire 434 can still provide electrosurgical cutting action to a polyp or tumor by capacitive coupling through the dielectric tube material. For example, coil or wire 434 acts as one plate of a capacitor. The thickness of tubing wall 428 between the embedded coil or wire 434 and its exterior acts as a dielectric of the capacitor. The target tissue site adjacent to the outer wall of tube 428 acts as the second plate of the capacitor. In this way, electrosurgical energy can be coupled to tissue that is not in direct contact with coil or wire 434, although it will not benefit from the gas assisted electrosurgical effect since no gas is flowing at this point.

Turning to FIG. 15C, a cross-section view of tube 428 at the portion of tube 428 indicated by reference number 15C-15C in FIG. 15A is shown in accordance with the present disclosure. As shown in FIG. 15C, at the portions of tube 428 where there are apertures 436, coil or wire 434 becomes exposed. When inert gas exits apertures 436, the electrosurgical energy provided by the exposed portion of coil or wire 434 will create a gas assisted electrosurgical effect that can be used to remove a polyp. As compared to the embodiment with a coil over the gas distribution tube 302, a design with the gas distribution tube 428 over the coil or wire 434 will permit a smaller physical size, an important consideration for endoscopic applications. An oscillating motion of the gas distribution tube 428 and coil or wire 436, similar to that described above, will have similar benefit due to the changing positions of direct contact with the exposed coil or wire 436 with the polyp or tumor 350.

It is to be appreciated that in other embodiments, electrosurgical snare device 402 may be configured to have coil or wire 434 disposed on and coupled to the outer walls of tube 428. This may be advantageous because if coil or wire 434 is disposed on the outer walls of tube 428, then coil or wire 434 will have increased contact with the polyp or tumor it is applied to, and therefore, more electrosurgical energy can be applied to the polyp or tumor to increase the cutting efficiency of the electrosurgical snare device 402. For example, turning to FIG. 16A, an electrosurgical snare device 502 with a coil or wire 534 disposed and coupled to the outer wall of tube 528 is shown in accordance with the present disclosure.

Similar to the embodiments described above, an electrosurgical snare device 502 includes an applicator handle (not shown) coupled to a support tube or shaft 518. Shaft 518 supports end effector 520 which includes tube 528, where tube 528 includes apertures 536. Similar to the above described embodiments, electrosurgical snare device 502 is configured such that inert gas is provided to tube 528. In contrast to previous embodiments, electrosurgical snare device 502 includes a flexible coil or wire 536 capable of conducting electrosurgical energy, where coil or wire 536 is coupled to the outer wall of tube 528 positioned on the inside diameter of the snare loop.

Turning to FIG. 16B, a cross-sectional view of tube 528 at the portion of tube 528 indicated by reference number 16B-16B in FIG. 16A is shown in accordance with the present disclosure. As seen in FIG. 16B, coil or wire 536 is coupled to the outer wall of tube 528.

Turning to FIG. 16C, a cross-sectional view of tube 528 at the portion of tube 528 indicated by reference number 16C-16C in FIG. 16A is shown in accordance with the present disclosure. As seen in FIG. 16C, at the portions of tube 528 where there are apertures 536, coil or wire 534 becomes exposed. When inert gas exits apertures 536, the electrosurgical energy provided by the exposed portion of coil or wire 534 will create a gas assisted electrosurgical effect that can be used to remove a polyp or tumor.

It is to be appreciated that the inert gas supplied to the various tubes may be applied to one, open end of the tube while the other end of the tube is closed. Alternatively, gas may be applied to both ends of the tube. It is to be appreciated that to have a uniform gas distribution among each of the holes 536 along tube 528, the cross-sectional area of the tube 528 must be no less than the sum of the areas of all of the holes 536, assuming the inlet of gas to tube 528 is only from one end of the tube. If, however, the gas inlet is fed to both sides of the tube, this cross-sectional requirement of tube 528 can be cut in half, reducing its diameter. It is also possible to further reduce the diameter of tube 528 by gradually enlarging the diameter of holes 536 as they are progressively placed further away from the gas inlet point (s), compensating as the pressure loss inside tube 528 increases further away from the inlet point(s).

Figure 17A:
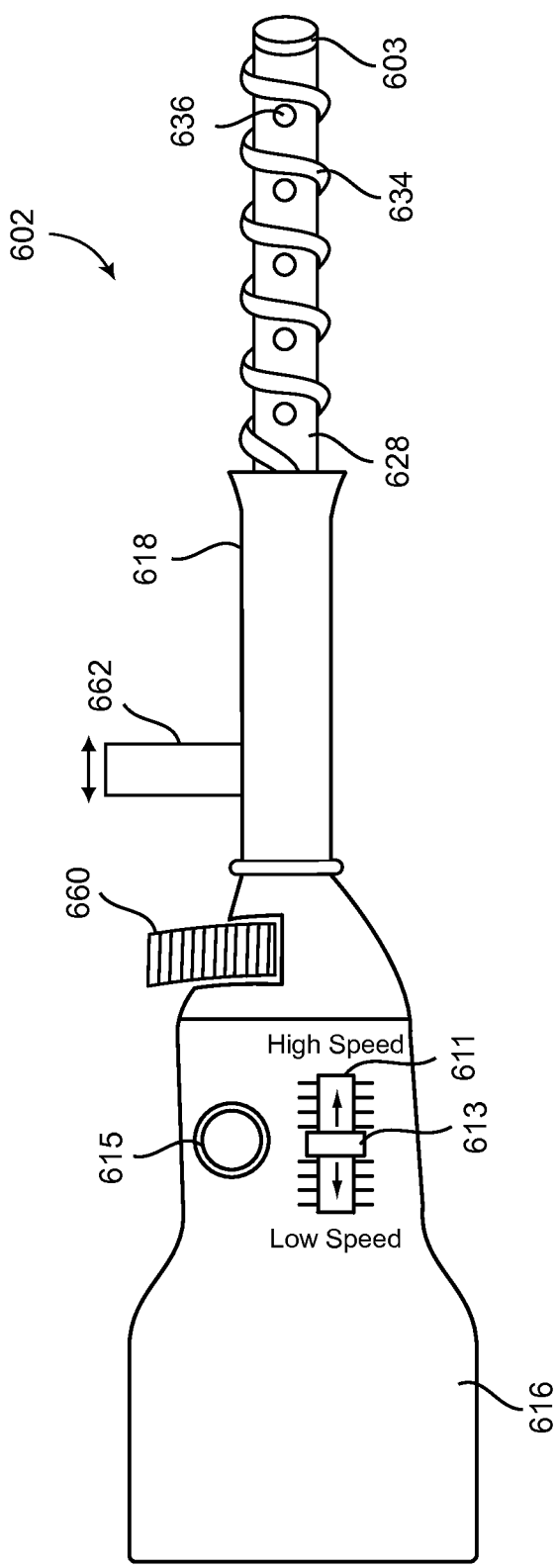
FIG. 17A shows an electrosurgical device with a linear realization in accordance with an embodiment of the present disclosure.

It is to be appreciated that an electrosurgical device similar to those described above in reference to FIGS. 1-16 may be configured for use in situations where a snare or loop cannot fit around a polyp or tumor. For example, turning to FIG. 17, an electrosurgical device 602 is shown with a linear realization in accordance with an embodiment of the present disclosure.

Electrosurgical device 602 includes applicator handle 616, which is coupled to support tube or shaft 618. Shaft 618 supports tube 628. Disposed on applicator handle 616 are button 615 and selector 613, where selector 613 is disposed on track 611. Disposed on tube 618 is lever 662. Wrapped around tube 628 is electrically conducting coil 634, e.g. a rigid spring. Furthermore, tube 628 includes apertures 636 incrementally disposed between the individual coils of coil 634. Disposed on the distal end of tube 628 is cap 603.

Tube 628 is made from a rigid non-conducting material, i.e., an electrically insulating material, and is configured to provide inert gas to apertures 636 and provide mechanical support for the coil 634. Also, cap 603 is configured such that the inert gas provided to tube 628 cannot escape from tube 628 other than from apertures 636. Furthermore, coil 634 is configured to provide electrosurgical energy to the inert gas exiting apertures 636 to create a gas assisted electrosurgical effect at each aperture.

Lever 662 is configured such that when lever 662 is pulled toward the distal end of electrosurgical device 602 the length of tube 628 that protrudes from tube 618 will be increased. Alternatively, when lever 662 is pulled toward the proximal end of electrosurgical device 602, the length of tube 628 that protrudes from tube 618 will be decreased. Additionally, thumbwheel 660 is configured such that when thumbwheel 660 is rotated tube 628 is also rotated. When tube 628 is rotated via thumbwheel 660, apertures 636 rotate as well to enable an operator to apply the plasma jets in 360 degrees of direction. It is to be appreciated that the thumbwheel 660 may be manipulated to cause a back and forth rotational motion of the tube 628 for tissue removal.

In some embodiments, button 615 is configured such that when button 615 is pressed, tube 628 will oscillate up and down. In other words, when button 615 is pressed, tube 628 will be extended for a predetermined length and then retracted to its original position. The oscillation of tube 628 may be achieved by a motor or actuator disposed in applicator handle 616 (not shown) coupled to the tube 628. It is to be appreciated that in this embodiment, lever 662 may be used to choose the maximal length tube 628 is allowed to extend when button 615 is pressed. Furthermore, selector 613 is configured such that if selector 613 is pulled along track 611 toward tube 618 or away from tube 618, the speed with which tube 628 oscillates will be increased or decreased.

In alternative embodiments, button 615 may be configured such that when button 615 is pressed, coil 634 will be extended along tube 628 for a predetermined length and then retracted to its original position. This extension and retraction of coil 634 will continue cyclicly, causing coil 634 to oscillate along tube 628. The oscillation of coil 634 may be achieved by a motor or actuator disposed in applicator handle 616 coupled to the coil 634. Furthermore, in this embodiment, selector 613 is configured such that if selector 613 is pulled along track 611 toward tube 618 or away from tube 618, the speed with which coil 634 moves along tube 628 will be increased or decreased.

In use, electrosurgical device 602 may be used in several ways to remove a polyp or tumor. For example, thumbwheel 660 may be used to direct apertures 636 in the direction of the polyp or tumor and lever 662 may be used to extend tube 628 to a desired length. Then, electrosurgical energy can be applied to coil 634 and inert gas can be provided to apertures 636. The combination of electrosurgical energy and inert gas will create a gas assisted electrosurgical effect at each aperture. Then, the user can oscillate electrosurgical device 602 in a reciprocating, saw like manner to remove the polyp or tumor. Additionally, the user can manipulate the electrosurgical device 602 to file any remaining tissue of the polyp or tumor after removal, i.e., to make smooth the area where the polyp or tumor was removed in relation to the surrounding tissue. Alternatively, in embodiments where button 615 is configured to oscillate tube 628 in the manner described above, the user can press button 615 and hold tube 628 against the polyp or tumor to remove the polyp or tumor. Alternatively, in embodiments where button 615 is configured to oscillate coil 634 along tube 628 in the manner described above, the user can pressed button 615 and hold tube 628 against the polyp or tumor to remove the polyp or tumor.

Figure 17B:
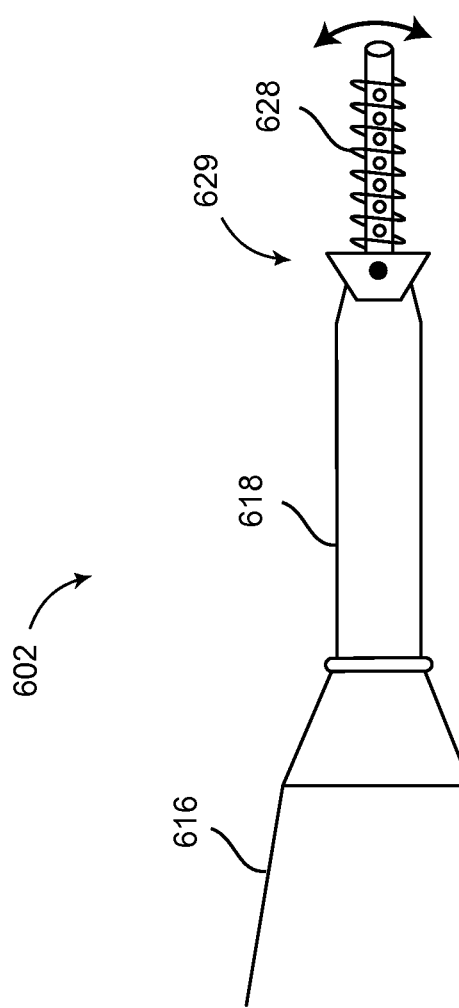
FIG. 17B shows an electrosurgical device with an articulating mechanism in accordance with another embodiment of the present disclosure.

In a further embodiment, an articulating mechanism 629, shown in FIG. 17B, is provided that is configured to allow tube 628 to move in an up and down planar motion. As described above, the articulating mechanism 629 may be a hinge, joint or the like.

It is to be appreciated that the surface area of the coil in the electrosurgical snare devices of the present disclosure will effect the overall impedance of the device as seen by an electrosurgcial generator. Therefore, in various embodiments, the impedance of the coil is determined and associated to the device. In one embodiment, the determined impedance is placed on a tag, sticker or the like on the device and used to calibrate the electrosurgical generator so the impedance of the generator matches the impedance of the electrosurgical snare device.

In another embodiment, the determined impedance is programmed, stored, written to, etc., in a memory device in the connector 108 of the electrosurgical snare device. When the connector 108 is coupled to the generator 104, at least one processor, or appropriate component, of the generator 104 reads the determined impedance from the connector 108 and auto-tunes certain components of the generator to calibrate the generator for a specific handpiece. Such a connector and auto-calibration system is disclosed and described in commonly owned U.S. application Ser. Nos. 13/802,572 and 14/715,847, the contents of which are hereby incorporated by reference in their entireties.

It is to be appreciated that the various features shown and described are interchangeable, that is, a feature shown in one embodiment may be incorporated into another embodiment.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudocode, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical device comprising:
a housing having a longitudinal axis; a support shaft attached to a distal end of the housing, the support shaft having a longitudinal axis substantially aligned with the longitudinal axis of the housing;
a tube at least partially disposed in the support shaft, the tube including a plurality of apertures disposed along a length of the tube; and
an electrically conducting spring disposed around the tube, the electrically conducting spring including a plurality of coils spaced apart from each other, where a spacing of the coils coincides with a spacing of the plurality of apertures, the electrically conducting spring adapted to move along the tube such that at different points in time the plurality of coils are disposed over the plurality of apertures or between the plurality of apertures or between the plurality of apertures,
wherein a gas assisted electrosurgical effect is formed at each of the plurality of apertures when an inert gas flows through the tube and the electrically conducting spring is energized, the gas assisted effect being enhanced when the plurality of coils are disposed over the plurality of apertures and the gas assisted effect being reduced when the plurality of coils are disposed between the plurality of apertures.

2. The electrosurgical device of claim 1, wherein the tube is made of a rigid, electrically non-conducting material, the tube supporting the electrically conducting spring.

3. The electrosurgical device of claim 1, wherein the tube is configured to rotate to vary a direction of the plurality of apertures.

4. The electrosurgical device of claim 1, wherein the tube is configured to move along the longitudinal axis of the support shaft.

5. The electrosurgical device of claim 4, further comprising an actuator that is configured to oscillate the tube within the support shaft.

6. The electrosurgical device of claim 1, wherein the electrically conducting spring is configured to oscillate along the tube.

7. The electrosurgical device of claim 1, further comprising an articulating mechanism that is configured to articulate the tube at a distal end of the support shaft.

8. The electrosurgical device of claim 1, further comprising a connector that connects the electrically conducting spring to an electrical energy source and the tube to a gas source, the connector including a memory device that stores an impedance value of the electrically conducting spring.

9. The electrosurgical device of claim 1, further comprising at least one lumen disposed in the support shaft configured to remove debris from a distal end of the support shaft.

10. The electrosurgical device of claim 1, wherein the tube is configured as a loop at a distal end of the support shaft.

11. The electrosurgical device of claim 10, further comprising a positioning assembly configured to move the loop between an extended position and a retracted position.

12. The electrosurgical device of claim 10, wherein the tube is configured to rotate to vary a direction of the plurality of apertures.

13. The electrosurgical device of claim 10, wherein the electrically conducting spring is configured to oscillate along the tube.

14. The electrosurgical device of claim 10, further comprising an articulating mechanism that is configured to articulate the loop at the distal end of the support shaft.

* * * * *